US010980822B2

(12) United States Patent
Kim

(10) Patent No.: US 10,980,822 B2
(45) Date of Patent: Apr. 20, 2021

(54) MEDICINAL COMPOSITION COMPRISING SGLT-2 INHIBITOR AND ANGIOTENSIN RECEPTOR BLOCKER

(71) Applicant: AUTOTELIC BIO INC., Chungcheongbuk-do (KR)

(72) Inventor: Tae-Hun Kim, Sejong (KR)

(73) Assignee: AUTOTELIC BIO INC., Chungcheongbuk-do (KR)

( * ) Notice: Subject to any disclaimer, the term of this patent is extended or adjusted under 35 U.S.C. 154(b) by 0 days.

(21) Appl. No.: 16/485,888

(22) PCT Filed: Aug. 31, 2018

(86) PCT No.: PCT/KR2018/010110
§ 371 (c)(1),
(2) Date: Aug. 14, 2019

(87) PCT Pub. No.: WO2019/059557
PCT Pub. Date: Mar. 28, 2019

(65) Prior Publication Data
US 2020/0054656 A1 Feb. 20, 2020

(30) Foreign Application Priority Data

Sep. 19, 2017 (KR) ........................ 10-2017-0120311
Jun. 28, 2018 (KR) ........................ 10-2018-0075025

(51) Int. Cl.
| | | |
|---|---|---|
| A61K 31/70 | (2006.01) | |
| A61K 31/4178 | (2006.01) | |
| A61P 3/10 | (2006.01) | |
| A61P 9/12 | (2006.01) | |
| A61K 9/20 | (2006.01) | |

(52) U.S. Cl.
CPC .......... *A61K 31/70* (2013.01); *A61K 31/4178* (2013.01); *A61P 3/10* (2018.01); *A61P 9/12* (2018.01); *A61K 9/2018* (2013.01); *A61K 9/2054* (2013.01)

(58) Field of Classification Search
CPC .. A61K 31/70; A61K 31/4178; A61K 9/2018; A61P 3/10; A61P 9/12
USPC ............................................... 514/23
See application file for complete search history.

(56) References Cited

FOREIGN PATENT DOCUMENTS

| | | |
|---|---|---|
| JP | 2006-501187 A | 1/2006 |
| JP | 2012-176920 A | 9/2012 |
| KR | 10-2002-0063876 A | 8/2002 |
| KR | 10-2007-0098811 A | 10/2007 |
| KR | 10-2010-0103874 A | 9/2010 |
| KR | 10-2015-0046125 A | 4/2015 |
| KR | 10-2016-0132887 A | 11/2016 |
| KR | 10-2018-0011842 A | 2/2018 |
| RU | 2464014 C2 | 10/2012 |
| WO | WO-2008/044862 A1 | 4/2008 |

OTHER PUBLICATIONS

Schagen et al. Discovering the link between nutrition and skin aging. Dermato-Endocrinology, 4:3, 298-307, 2012. (Year: 2012).*
Choi Cl. Sodium-Glucose Cotransporter 2 (SGLT2) Inhibitors from Natural Products: Discovery of Next-Generation Antihyperglycemic Agents. Molecules 2016, 21, 1136, p. 1-12. (Year: 2016).*
Alexander W. Hypertension: Is It Time to Replace Drugs With Nutrition and Nutraceuticals? P & T 39(4): 291-295, 2014. (Year: 2014).*
Kasichayanula et al. Lack of Pharmacokinetic Interactions Between Dapagliflozin and Simvastatin, Valsartan, Warfarin, or Digoxin. Adv Ther (2012) 29(2): 163-177. (Year: 2012).*
Kawasoe et al. Mechanism of the blood pressure-lowering effect of sodium-glucose cotransporter 2 inhibitors in obese patients with type 2 diabetes. BMC Pharmacology and Toxicology (2017) 18:23, p. 1-10. Published online: Apr. 10, 2017. (Year: 2017).*
Osorio, H., et al.; "Effect of treatment with losartan on salt sensitivity and SGLT2 expression in hypertensive diabetic rats", Diabetes Research and Clinical Practice, 86, 2009, pp. 46-49.
International Search Report from corresponding PCT Application No. PCT/KR2018/010110, dated Mar. 13, 2019.
International Search Report from PCT Application No. PCT/KR2019/011539, dated Jan. 10, 2020.
Kalra, S., et al.; "Sodium-Glucose Cotransporter-2 Inhibition and the Glomerulus: A Review", Adv. Ther. Jul. 16, 2016, vol. 33, No. 9, pp. 1502-1518.

* cited by examiner

*Primary Examiner* — Yih-Horng Shiao
(74) *Attorney, Agent, or Firm* — Harness, Dickey & Pierce, P.L.C.

(57) ABSTRACT

Provided is a pharmaceutical composition comprising an antidiabetic agent and an antihypertensive agent as active ingredients.

5 Claims, 5 Drawing Sheets

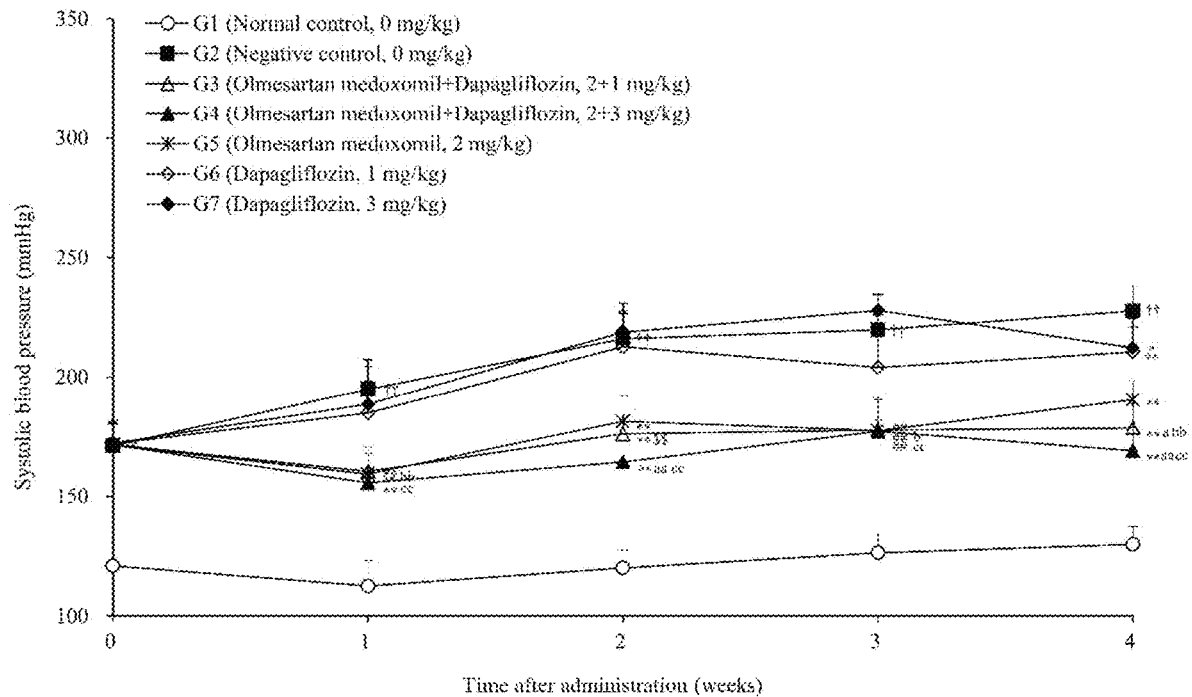

Each point represents the mean ± S.D., n=7~8
++ p<0.01, Significant difference from the normal control group (G1) by Student t-test.
* p<0.05, Significant difference from the negative control group (G2) by Dunnett's t-test.
** p<0.01, Significant difference from the negative control group (G2) by Dunnett's t-test.
# p<0.05, Significant difference from the negative control group (G2) by Steel's t-test.
p<0.01, Significant difference from the negative control group (G2) by Steel's t-test.
a p<0.05, Significant difference from the comparative substance1 group (G5) by Dunnett's t-test.
aa p<0.01, Significant difference from the comparative substance1 group (G5) by Dunnett's t-test.
b p<0.05, Significant difference from the comparative substance2 group1 (G6) by Student t-test.
bb p<0.01, Significant difference from the comparative substance2 group1 (G6) by Student t-test.
$$ p<0.01, Significant difference from the comparative substance2 group1 (G6) by Aspin-Welch t-test.
cc p<0.01, Significant difference from the comparative substance2 group2 (G7) by Student t-test.

FIG. 4

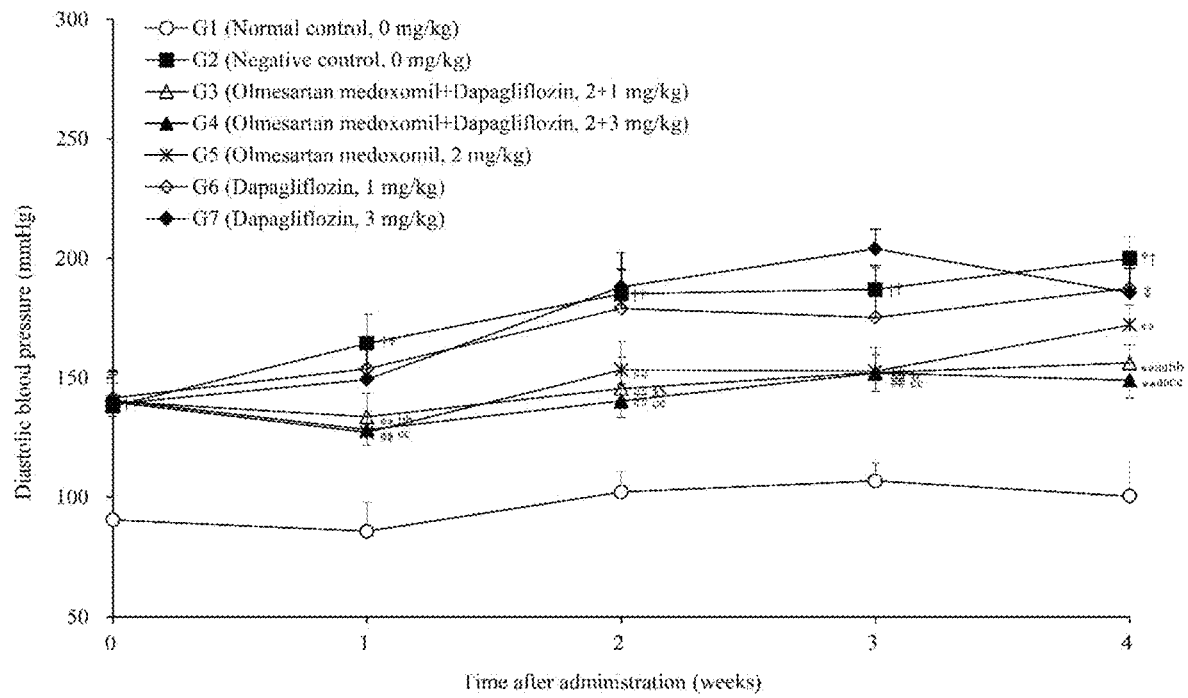

Each point represents the mean + S.D., n=7 ~ 8
††p<0.01, Significant difference from the normal control group (G1) by Student t-test.
*p<0.05, Significant difference from the negative control group (G2) by Dunnett's t-test.
**p<0.01, Significant difference from the negative control group (G2) by Dunnett's t-test.
p<0.01, Significant difference from the negative control group (G2) by Steel's t-test.
aap<0.01, Significant difference from the comparative substance1 group(G5) by Dunnett's t-test.
bp<0.05, Significant difference from the comparative substance2 group1 (G6) by Student t-test.
bbp<0.01, Significant difference from the comparative substance2 group1 (G6) by Student t-test.
$$p<0.01, Significant difference from the comparative substance2 group1 (G6) by Aspin-Welch t-test.
ccp<0.01, Significant difference from the comparative substance2 group2 (G7) by Student t-test.

FIG. 5

MEDICINAL COMPOSITION COMPRISING SGLT-2 INHIBITOR AND ANGIOTENSIN RECEPTOR BLOCKER

CROSS-REFERENCE TO RELATED APPLICATIONS

This application is a national phase application of PCT Application No. PCT/KR2018/010110, filed on Aug. 31, 2018, which claims benefit of Korean Patent Application Nos. 10-2017-0120311, filed on Sep. 19, 2017 and 10-2018-0075025, filed on Jun. 28, 2018. The entire disclosure of the applications identified in this paragraph are incorporated herein by references.

FIELD

The present invention relates to a pharmaceutical composition comprising an antidiabetic agent, such as an SGLT-2 inhibitor, and an antihypertensive agent such as an angiotensin receptor blocker. According to the present invention, the blood pressure lowering effect and patient compliance of an antidiabetic agent and an antihypertensive agent may be improved by formulating these agents in a single pharmaceutical composition.

BACKGROUND

Antihypertensive agents which are currently used include diuretics, sympatholytic drugs, calcium channel blockers (CCBs), angiotensin converting enzymes (ACEs) inhibitors, angiotensin receptor blockers (ARBs), renin inhibitors, vasodilators, etc.

Among such antihypertensive agents, angiotensin receptor blockers (hereinafter referred to as "ARB") are being used increasingly as antihypertensive agents due to their blood pressure lowering effect, ventricular function preservation effect and fibrosis prevention effect. As ARB drugs, losartan was developed, and since then valsartan, candesartan, irbesartan, telmisartan, eprosartan, olmesartan and the like have been developed and used as blood pressure lowering agents.

Meanwhile, as agents for treating diabetes which is a metabolic disorder, oral blood glucose lowering agents are used as well as insulin injections. In addition, drugs, such as AMP-activated protein kinase (AMPK) activators (e.g., metformin, etc.), dipeptidyl peptidase (DPP)-4 inhibitors (e.g., sitagliptin, linagliptin, saxagliptin, vildagliptin, etc.), SGLT (sodium-dependent glucose cotransporter)-2 inhibitors (e.g., dapagliflozin, empagliflozin, canagliflozin, etc.) are used as oral blood glucose lowering agents.

However, the blood pressure lowering effect of an SGLT-2 inhibitor or a combination of an SGLT-2 inhibitor and an ARB drug has not been reported.

SUMMARY

Technical Problem

The present invention is intended to improve the antihypertensive effect and patient compliance of the antidiabetic agent SGLT-2 inhibitor and the antihypertensive agent ARB by co-administering these agents.

Technical Solution

As a mean for solving the above technical task, a pharmaceutical composition of the present invention comprises the antidiabetic agent SGLT-2 inhibitor and the antihypertensive agent ARB.

Advantageous Effects

According to the present invention, an SGLT-2 inhibitor and an ARB act synergistically with each other, thereby improving the blood pressure lowering effect and patient compliance.

Diabetes and hypertension often occur together in patients, and antihypertensive agents with different mechanisms are often co-administered to hypertensive patients. Accordingly, a large number of drugs to be administered to patients with hypertension or patients with both hypertension and diabetes are present, resulting in compliance problems.

In particular, hypertensive or diabetic patients should continuously take antihypertensive agents and/or antidiabetic agents over a long period of time, and hence the problem of compliance caused by a large number of drugs to be administered is a serious consideration for hypertensive or diabetic patients.

According to the present invention, the compliance of patients with both hypertension and diabetes can be greatly improved by formulating an antidiabetic agent and an antihypertensive agent in a single pharmaceutical composition having a blood pressure lowering effect.

BRIEF DESCRIPTION OF THE DRAWINGS

FIG. 4 graphically shows the results of measuring systolic blood pressure in each test group in Experimental Example 2.

FIG. 5 graphically shows the results of measuring diastolic blood pressure in each test group in Experimental Example 2.

DETAILED DESCRIPTION

Figure 1:
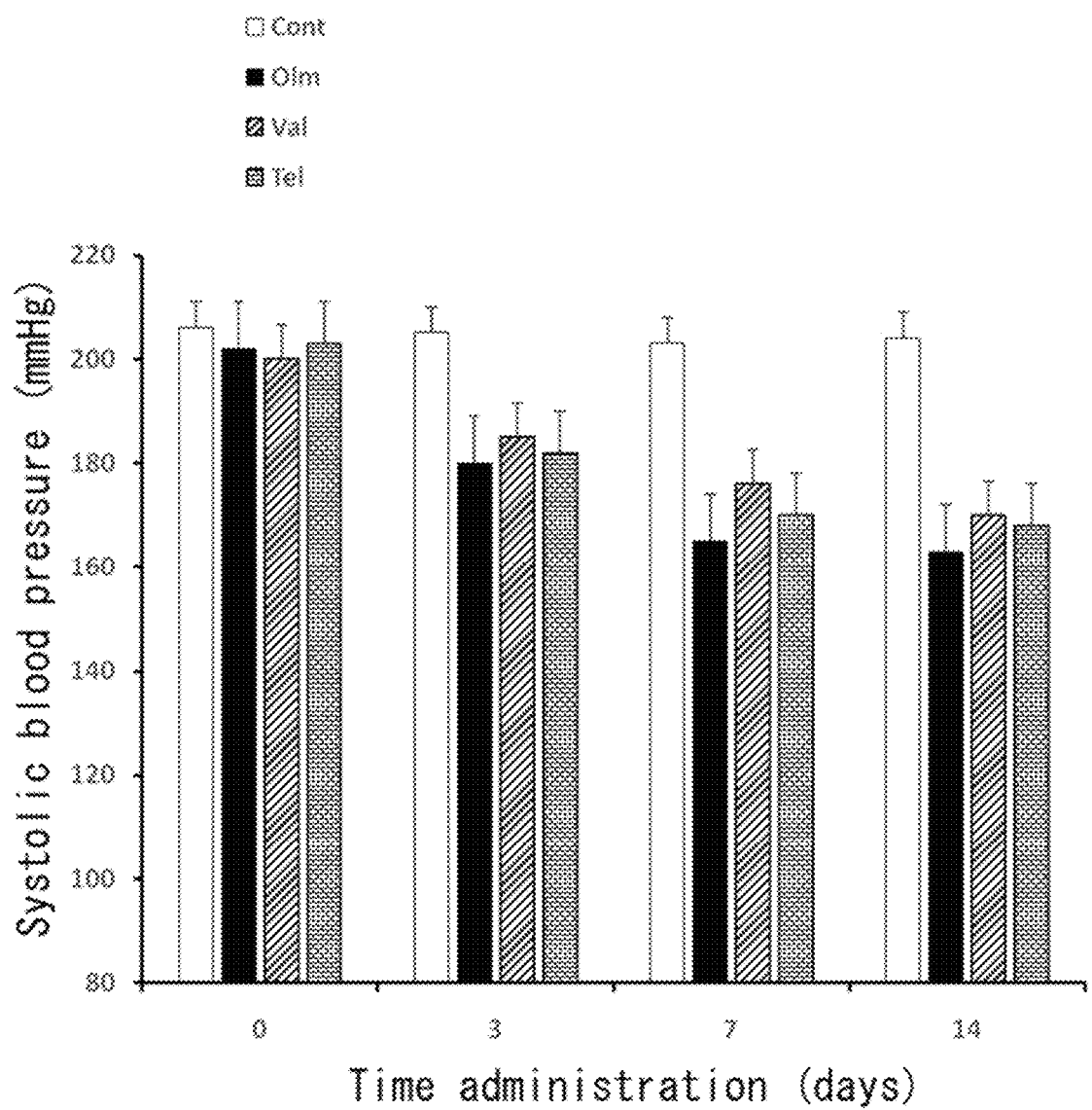
FIG. 1 graphically shows the blood pressures measured in groups administered with various ARB drugs alone and in a control group in Experimental Example 1.

The present invention is directed to a pharmaceutical composition comprising the antidiabetic agent SGLT-2 inhibitor and the antihypertensive agent angiotensin receptor blocker (ARB) as active ingredients.

In the present invention, dapagliflozin, empagliflozin, canagliflozin or the like may be used as the SGLT-2 inhibitor, and among them, dapagliflozin is preferably used.

In the present invention, losartan, valsartan, candesartan, irbesartan, telmisartan, eprosartan, olmesartan or the like may be used as the ARB, and among them, olmesartan is preferably used.

An antidiabetic agent and an antihypertensive agent, which may be contained in the pharmaceutical composition of the present invention, may be presented as a free base form thereof, or a pharmaceutically acceptable salt or solvate form, or a pharmaceutically acceptable ester form thereof.

Those skilled in the art can understand that, for example, dapagliflozin or a pharmaceutically acceptable salt or solvate thereof may be used as the SGLT-2 inhibitor in the present invention. In addition, those skilled in the art can understand that, for example, olmesartan or a pharmaceutically acceptable salt thereof or a pharmaceutically acceptable ester thereof (e.g., olmesartan medoxomil, olmesartan cilexetil, etc.) may be used as the antihypertensive agent.

The pharmaceutical composition according to the present invention has an improved blood pressure lowering effect as confirmed in the Example section below. Thus, the pharmaceutical composition of the present invention is useful as an antihypertensive agent.

In particular, since the SGLT-2 inhibitor has been originally used for the treatment of diabetes, the pharmaceutical composition of the present invention is effective not only for the treatment of hypertension, but also for the treatment of diabetes. Therefore, the pharmaceutical composition of the present invention may be used to treat both hypertension and diabetes, and thus the pharmaceutical composition of the present invention may be advantageously administered not only to hypertensive patients, but also to patients with both hypertension and diabetes.

In general, diabetes and hypertension often occur together in patients, and antihypertensive agents with different mechanisms are often co-administered to hypertensive patients. Accordingly, a large number of drugs to be administered to patients with hypertension or patients with both hypertension and diabetes are present, resulting in compliance problems. In particular, hypertensive or diabetic patients should continuously take antihypertensive agents and/or antidiabetic agents over a long period of time, and hence the problem of compliance caused by a large number of drugs to be administered is a serious consideration for hypertensive or diabetic patients.

According to the present invention, the compliance of patients with hypertension or patients with both hypertension and diabetes can be greatly improved by formulating an antidiabetic agent and an antihypertensive agent in a single pharmaceutical composition exhibiting a blood pressure lowering effect.

The pharmaceutical composition of the present invention may be formulated into various oral dosage forms. For example, the pharmaceutical composition of the present invention may be formulated into various oral dosage forms, including solid or liquid formulations, such as tablets, capsules, liquids, granules, powders, emulsions, suspensions, syrups and the like. Preferably, it may be formulated into a tablet.

The pharmaceutical composition of the present invention may be formulated as sustained-release formulations or enteric-coated formulations so as to exhibit various drug release profiles, and may also be formulated into various dosage forms, including a single-layer tablet, a multi-layer tablet composed of two or more layers, a core tablet, and the like.

A tablet-type pharmaceutical composition according to the present invention may be prepared by compression into tablets with conventional additives, for example, an excipient, a binder, a disintegrant, a lubricant and the like. As usable additives, excipients (diluents) that may be used include, for example, lactose, starch, white sugar, mannitol, sorbitol, inorganic salts, crystalline cellulose, and the like. Binders that may be used include, for example, white sugar, glucose, starch, gelatin, sodium carboxymethyl cellulose, methyl cellulose, gum Arabic, ethyl cellulose, hydroxypropyl methyl cellulose, and the like. Disintegrants that may be used include, for example, sodium croscarmellose, calcium carmellose, polyvinylpyrrolidone, and the like. Lubricants that may be used include, for example, magnesium stearate, calcium stearate, talc, and the like.

Tablets may be easily prepared by those skilled in the art according to conventional methods known in the pharmaceutical formulation field, for example, a direct powder compression method, a wet granule compression method, a dry granule compression method, and the like.

The dose of each active ingredient of the present invention may be determined based on the known dose of each active ingredient. However, considering that the two active ingredients of the present invention exhibit a synergistic effect with each other, the dose of each active ingredient can be reduced as compared with when it is administered alone.

For example, the composition of the present invention may be formulated such that the SGLT-2 inhibitor is administered to an adult patient at a dose of 0.1 to 200 mg/day and the ARB drug is administered at a dose of 1 to 200 mg.

Hereinafter, the present invention will be described in detail with reference to examples. However, these examples are only illustrative of the present invention and the spirit or scope of the present invention is not limited by these examples.

EXAMPLES

Experimental Example 1

2-Week Evaluation of Blood Pressure Lowering Effect of Drugs

A. Experimental Method

As experimental animals, 10-week-old spontaneously hypertensive rats (SHRs) which are hypertensive disease models were used. The SHR rats are rats derived from Wistar Kyoto WKY) rats with normal blood pressure, and are rats that spontaneously develop hypertension with aging without any artificial treatment. The SHR rats are optimal animal models for human primary hypertension (essential hypertension) with a systolic blood pressure of about 200 mmHg or more.

The blood pressure in the experimental animals was measured using a CODA-6 system (Kent Scientific Corp.) which is a non-invasive blood pressure (NIBP) measurement system. The hypersensitive rats were placed and stabilized in restrainers for 15 minutes, and then the blood pressure thereof was measured 6 times and the average value thereof was used as a blood pressure measurement. The blood pressure in the tail of each experimental animal was measured before this experiment, and only hypertensive rats with a systolic blood pressure of 190 mmHg or higher were used in this experiment.

The rats were divided into total 7 groups according to the kind of drug to be administered, and five rats were randomly assigned to each group. The groups administered with each drug are as follows:

(1) a control group not administered with any drug;
(2) a group administered with 1 mg/kg/day of olmesartan medoxomil alone;
(3) a group administered with 4 mg/kg/day of valsartan alone;
(4) a group administered with 4 mg/kg/day of telmisartan alone;

(5) a group administered with a combination of 1 mg/kg/day of olmesartan medoxomil+1 mg/kg/day of dapagliflozin;

(6) a group administered with a combination of 4 mg/kg/day of valsartan+1 mg/kg/day of dapagliflozin;

(7) a group administered with a combination of 4 mg/kg/day of telmisartan+1 mg/kg/day of dapagliflozin.

(*In this Example, a dapagliflozin propylene glycol hydrate corresponding to 1 mg of dapagliflozin was administered actually).

For drug administration, each drug was administered to each rat once a day at a predetermined dose at the same time every morning. Considering that the amounts of antihypertensive drugs used in humans are different, the antihypertensive drugs were administered at different doses.

Each drug was repeatedly administered once a day for 2 weeks (14 days), and blood pressure was measured 2 hours after daily administration of each drug.

B. Results of Blood Pressure Measurement

For the group administered with each antihypertensive drug alone, the blood pressure before administration of the drug and at 3rd day, 7th day and 14th day after administration of the antihypertensive drug alone was measured six times and averaged, and the average value of five rats for each group was calculated. The results are shown in FIG. 1.

In addition, for the group co-administered with the antihypertensive drug and dapagliflozin, the blood pressures before administration of the drug and at 3rd day, 7th day and 14th day after co-administration were measured six times and averaged, and the average value of five rats for each group was calculated. The results are shown in FIG. 2.

Figure 3:
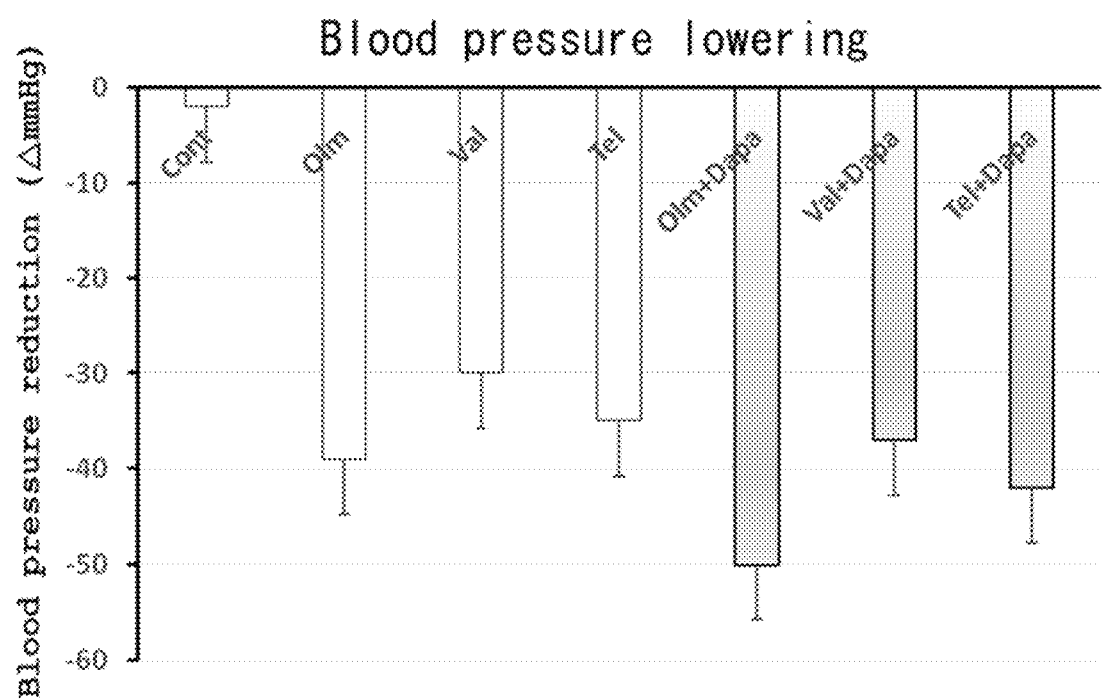
FIG. 3 graphically shows the results of measuring the size of blood pressure reduction in each test group in Experimental Example 1.

FIG. 3 shows the size of blood pressure reduction, obtained by measuring the blood pressure in each test group at 14th day after drug administration and comparing the measured blood pressure with the initial blood pressure.

As shown in FIG. 1, the control group (Cont) not administered with any drug showed little or no reduction in blood pressure, whereas the groups administered with each antihypertensive drug alone showed reduction in blood pressure.

Figure 2:
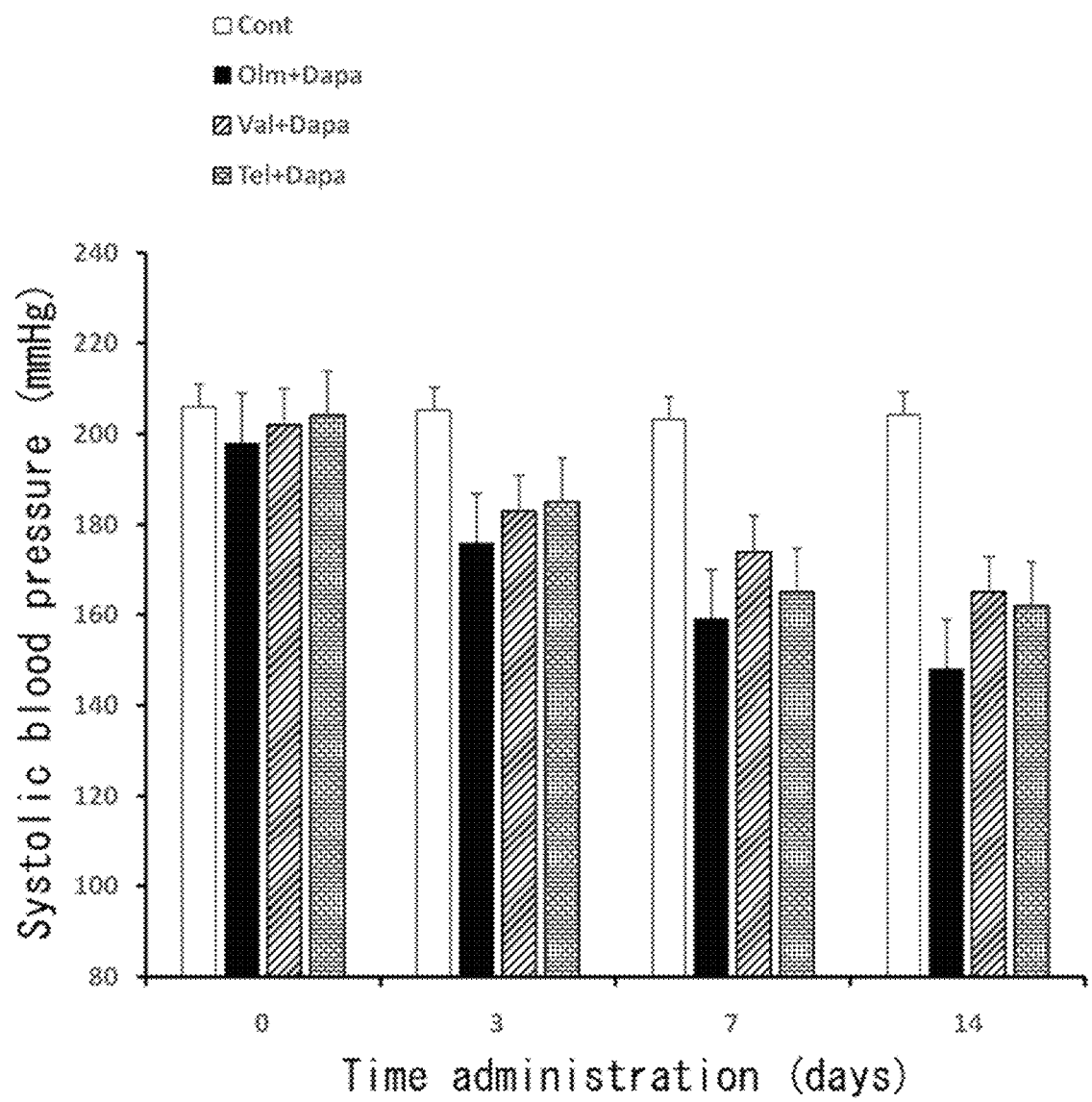
FIG. 2 graphically shows the blood pressures measured in groups co-administered with various ARB drugs and an SGLT-2 inhibitor and in a control group in Experimental Example 1.

As shown in FIG. 2, it could be seen that the blood pressure in the group co-administered with dapagliflozin and each antihypertensive agent was generally more reduced with the passage of time than that in the group administered with each antihypertensive drug alone.

Namely, the groups administered with each of olmesartan medoxomil, valsartan and telmisartan alone for 14 days showed blood pressure reductions of 39 mmHg, 30 mmHg and 35 mmHg, respectively, at 14th day after drug administration, compared to before drug administration. However, the groups administered with each of olmesartan medoxomil, valsartan and telmisartan in combination with dapagliflozin for 14 days showed significant reductions in blood pressure of 50 mmHg, 37 mmHg and 42 mmHg, respectively, at 14th day after drug administration, compared to before drug administration.

Table 1 below shows the systolic blood pressure values of each group, measured immediately before drug administration and at 14th day after drug administration.

TABLE 1

Systolic blood pressure values (unit: mmHg) measured for each group

| Groups | Blood pressure immediately before administration | Blood pressure at 14th day after administration | Size of blood pressure reduction |
|---|---|---|---|
| Control | 206 | 204 | 2 |
| Olmesartan medoxomil alone | 202 | 163 | 39 |
| Valsartan alone | 200 | 170 | 30 |
| Telmisartan alone | 203 | 168 | 35 |
| Olmesartan medoxomil + dapagliflozin | 198 | 148 | 50 |
| Valsartan + dapagliflozin | 202 | 165 | 37 |
| Telmisartan + dapagliflozin | 204 | 162 | 42 |

FIG. 3 shows the size of blood pressure reduction, obtained by measuring the blood pressure value of each group after 14 days of drug administration and comparing the measured blood pressure value with the initial blood pressure immediately before drug administration. As shown therein, it can be seen that the blood pressure lowering effect when each ARB drug was co-administered with dapagliflozin was greater than that when each ARB drug was administered alone.

In particular, it can be seen that the blood pressure lowering effect more significantly increased when olmesartan medoxomil and dapagliflozin were co-administered, compared to when another antihypertensive drug with the same mechanism (i.e., valsartan or telmisartan) was co-administered with dapagliflozin.

Namely, the blood pressure lowering effect when the antihypertensive agent ARB drug and the antidiabetic agent SGLT-2 inhibitor, which may be administered orally, are co-administered is greater than that when the ARB is administered alone. In particular, co-administration of olmesartan medoxomil among ARB drugs with the antidiabetic agent dapagliflozin which may be administered orally can exhibit a greater blood pressure lowering effect in the treatment of hypertension.

Thus, when the two drugs are administered in combination to patients with both hypertension and diabetes, the treatment of diabetes and the treatment of hypertension can be simultaneously achieved and the antihypertensive effect can also be significantly increased.

In addition, even though other antihypertensive agent is not co-administered to a patient, a further improved blood pressure lowering effect can be achieved by co-administering the antidiabetic agent and the antihypertensive agent.

Experimental Example 2

4-Week Evaluation of Blood Pressure Lowering Effect

A. Experimental Method

As experimental animals, 6-week-old male SHR rats were used (however, WKY rats were used as a normal control).

A method for measurement of blood pressure is as follows: At about 30 minutes before measurement on each day, a vehicle (0.5% methyl cellulose aqueous solution) or a drug was administered (a normal control group and a negative control group were administered with only a vehicle alone), and before blood pressure measurement, a restrainer containing the animals were heated with an infrared lamp and a warm mat for about 10 minutes. The restrainer was placed on the animal heating unit of a blood pressure measurement system, and when the animals were confirmed to be stable, the blood pressure in the tail was measured 3 to 5 times by a non-invasive blood pressure measurement system and the measurements were averaged.

The rats were divided into total 7 groups according to the kind of drug to be administered, and eight rats were randomly assigned to each group. The groups administered with each drug are as follows:

(1) a normal control group (G1): a normal animal group;

(2) a negative control group (G2): a control group not administered with any drug;

(3) a group administered with test substance 1 (G3): a group administered with a combination of 2 mg/kg/day of olmesartan medoxomil+1 mg/kg/day of dapagliflozin;

(4) a group administered with test substance 2 (G4): a group administered with a combination of 2 mg/kg/day of olmesartan medoxomil+3 mg/kg/day of dapagliflozin;

(5) a group administered with comparative substance 1 (G5): a group administered with 2 mg/kg/day of olmesartan medoxomil alone;

(6) a group administered with comparative substance 2 (G6): a group administered with 1 mg/kg/day of dapagliflozin alone;

(7) a group administered with comparative substance 2 (G7): a group administered with 3 mg/kg/day of dapagliflozin alone.

(* In this Experimental Example, dapagliflozin was administered in an anhydride form, not a solvate form).

For drug administration, each drug was forcibly administered into the rat's stomach through a disposable syringe with an oral zonde at a predetermined dose at the same time every day. As test substances, olmesartan medoxomil was administered, and then immediately dapagliflozin was administered. The doses of the antihypertensive drug and the antidiabetic drug were determined considering the doses to be applied in clinical practice.

Each drug was repeatedly administered once a day for 4 weeks (a total of 29 times), and blood pressure was measured once a week.

B. Results of Systolic Blood Pressure Measurement

Systolic blood pressure values measured for each group are shown in FIG. 4 and Table 2 below.

The mean systolic blood pressure of the normal control group (G1) was in the range of 113 to 130 mmHg.

The mean systolic blood pressure of the negative control group (G2) was in the range of 171 to 228 mmHg and showed a tendency to increase with time. The negative control group showed a significant increase in blood vessel at all measurement time points compared to the normal control group (G1) ($p<0.01$).

It was shown that the mean systolic blood pressure values of the group administered with the 2:1 mixture of olmesartan medoxomil and dapagliflozin (G3) and the group administered with the 2:3 mixture of olmesartan medoxomil and dapagliflozin (G4) were in the ranges of 160 to 179 mmHg and 156 to 177 mmHg, respectively, and were statistically significantly lower than that of the negative control group (G2) ($p<0.01$: at 1st, 2nd, 3rd and 4th week after administration).

It was shown that the mean systolic blood pressure of the group administered with 2 mg/kg/day of olmesartan medoxomil (G5) was in the range of 159 to 190 mmHg and was statistically significantly lower than that of the negative control group (G2) ($p<0.01$: at 1st, 2nd, 3rd and 4th week after administration).

It was shown that the mean systolic blood pressure value of the group administered with the 2:1 mixture of olmesartan medoxomil and dapagliflozin (G3) was statistically significantly lower than that of the group administered with 2 mg/kg/day of olmesartan medoxomil (G5) ($p<0.05$: at 4th week after administration).

It was shown that the mean systolic blood pressure value of the group administered with the 2:3 mixture of olmesartan medoxomil and dapagliflozin (G4) was statistically significantly lower than that of the group administered with 2 mg/kg/day of olmesartan medoxomil (G5) ($p<0.01$: at 2nd and 4th week after administration).

It was shown that the mean systolic blood pressure value of the group administered with the 2:1 mixture of olmesartan medoxomil and dapagliflozin (G3) was statistically significantly lower than that of the group administered with 1 mg/kg/day of vildagliptin (G6) ($p<0.05$: at 3 weeks after administration; $p<0.01$: at 1, 2 and 4 week after administration).

TABLE 4

Systolic blood pressure values (unit: mmHg) measured for each group

| Groups | | Blood pressure immediately after administration | Blood pressure at 1st week after administration | Blood pressure at 2nd week after administration | Blood pressure at 3rd week after administration | Blood pressure at 4th week after administration |
|---|---|---|---|---|---|---|
| Normal control group (G1) | Mean | 121 | 113 | 120 | 126 | 130 |
| | S.D. | 9 | 11 | 7 | 8 | 7 |
| Negative control group (G2) | Mean | 171 | 195 | 216 | 220 | 228 |
| | S.D. | 11 | 9 | 12 | 9 | 11 |
| 2 mg olmesartan medoxomil + 1 mg dapagliflozin (G3) | Mean | 172 | 160 | 176 | 178 | 179 |
| | S.D. | 10 | 10 | 6 | 14 | 10 |
| 2 mg olmesartan medoxomil + 3 mg dapagliflozin (G4) | Mean | 172 | 156 | 164 | 177 | 169 |
| | S.D. | 10 | 12 | 12 | 5 | 10 |
| 2 mg olmesartan medoxomil (G5) | Mean | 171 | 159 | 181 | 178 | 190 |
| | S.D. | 9 | 9 | 11 | 13 | 8 |
| 1 mg dapagliflozin (G6) | Mean | 172 | 185 | 213 | 204 | 211 |
| | S.D. | 9 | 13 | 18 | 22 | 11 |
| 3 mg dapagliflozin (G7) | Mean | 172 | 189 | 219 | 228 | 212 |
| | S.D. | 8 | 19 | 8 | 7 | 13 |

It was shown that the mean systolic blood pressure value of the group administered with the 2:3 mixture of olmesartan medoxomil and dapagliflozin (G4) was statistically significantly lower than that of the group administered with 3rd mg/kg/day of vildagliptin (G7) ($p<0.01$: at 1st, 2nd, 3rd and 4th week after administration).

C. Results of Diastolic Blood Pressure Measurement

Diastolic blood pressure values measured for each group are shown in FIG. 5 and Table 3 below.

TABLE 3

Diastolic blood pressure values (unit: mmHg) measured for each group

| Groups | | Blood pressure immediately after administration | Blood pressure at 1st week after administration | Blood pressure at 2nd week after administration | Blood pressure at 3rd week after administration | Blood pressure at 4th week after administration |
|---|---|---|---|---|---|---|
| Normal control group (G1) | Mean | 91 | 86 | 102 | 107 | 101 |
| | S.D. | 11 | 12 | 9 | 7 | 14 |
| Negative control group (G2) | Mean | 138 | 164 | 185 | 187 | 200 |
| | S.D. | 13 | 12 | 10 | 9 | 9 |
| 2 mg olmesartan medoxomil + 1 mg dapagliflozin (G3) | Mean | 140 | 134 | 146 | 152 | 156 |
| | S.D. | 12 | 9 | 8 | 15 | 10 |
| 2 mg olmesartan medoxomil + 3 mg dapagliflozin (G4) | Mean | 141 | 128 | 140 | 152 | 149 |
| | S.D. | 13 | 10 | 13 | 7 | 8 |
| 2 mg olmesartan medoxomil (G5) | Mean | 140 | 127 | 153 | 153 | 172 |
| | S.D. | 12 | 9 | 12 | 10 | 8 |
| 1 mg dapagliflozin (G6) | Mean | 142 | 154 | 179 | 175 | 187 |
| | S.D. | 11 | 10 | 23 | 22 | 8 |
| 3 mg dapagliflozin (G7) | Mean | 139 | 149 | 188 | 204 | 186 |
| | S.D. | 14 | 17 | 7 | 8 | 15 |

The mean diastolic blood pressure of the normal control group (G1) was in the range of 81 to 107 mmHg.

The mean diastolic blood pressure of the negative control group (G2) was in the range of 138 to 200 mmHg and showed a tendency to increase with time. The negative control group showed a significant increase in blood vessel at all measurement time points compared to the normal control group (G1) ($p<0.01$).

It was shown that the mean diastolic blood pressure values of the group administered with the 2:1 mixture of olmesartan medoxomil and dapagliflozin (G3) and the group administered with the 2:3 mixture of olmesartan medoxomil and dapagliflozin (G4) were in the ranges of 134 to 156 mmHg and 128 to 152 mmHg, respectively, and were statistically significantly lower than that of the negative control group (G2) ($p<0.01$: at 1st, 2nd, 3rd and 4th week after administration).

It was shown that the mean diastolic blood pressure of the group administered with 2 mg/kg/day of olmesartan medoxomil (G5) was in the range of 127 to 172 mmHg and was statistically significantly lower than that of the negative control group (G2) ($p<0.01$: at 1st, 2nd, 3rd and 4th week after administration).

It was shown that the mean diastolic blood pressure values of the group administered with the 2:1 mixture of olmesartan medoxomil and dapagliflozin (G3) and the group administered with the 2:3 mixture of olmesartan medoxomil and dapagliflozin (G4) were all statistically significantly lower than that of the group administered with 2 mg/kg/day of olmesartan medoxomil (G5) ($p<0.01$: at 4th week after administration).

It was shown that the mean diastolic blood pressure values of the group administered with the 2:1 mixture of olmesartan medoxomil and dapagliflozin (G3) was statistically significantly lower than that of the group administered with 1 mg/kg/day of vildagliptin (G6) ($p<0.05$: at 3rd week after administration; $p<0.01$: at 1st, 2nd and 4th week after administration).

It was shown that the mean diastolic blood pressure values of the group administered with the 2:3 mixture of olmesartan medoxomil and dapagliflozin (G4) was statistically significantly lower than that of the group administered with 3 mg/kg/day of vildagliptin (G7) ($p<0.01$: at 1st, 2nd, 3rd and 4th weeks after administration).

From the above results of the Experimental Examples, it can be seen that co-administration of the olmesartan drug with dapagliflozin exhibited a synergistic effect and showed a greater blood pressure lowering effect than administration of the olmesartan drug alone.

Formulation Example 1

Preparation of Tablet

Contents of Components in One Tablet

Dapagliflozin propylene glycol hydrate: 6.15 mg

Olmesartan medoxomil: 40 mg

Microcrystalline cellulose: 100 mg

Mannitol: 100 mg

Hydroxypropyl methyl cellulose: 10 mg

Carboxymethylcellulose calcium: 10 mg

Magnesium stearate: 3 mg

According to the above-described composition, dapagliflozin propylene glycol hydrate, olmesartan medoxomil, microcrystalline cellulose, and mannitol are mixed with one another, and hydroxypropyl methyl cellulose dissolved in ethanol is added thereto as a binder. The resulting mixture is prepared into granules by a wet granulation method. Carboxymethyl cellulose calcium and magnesium stearate are added to and mixed with the granules, and then the mixture was compressed into a tablet.

Formulation Example 2

Preparation of Tablet

Contents of Components in One Tablet
Dapagliflozin anhydride: 10 mg
Olmesartan medoxomil: 40 mg
Microcrystalline cellulose: 100 mg
Mannitol: 100 mg
Hydroxypropyl methyl cellulose: 10 mg
Carboxymethylcellulose calcium: 10 mg
Magnesium stearate: 3 mg According to the above-described composition, dapagliflozin, olmesartan medoxomil, microcrystalline cellulose, and mannitol are mixed with one another, and hydroxypropyl methyl cellulose dissolved in ethanol is added thereto as a binder. The resulting mixture is prepared into granules by a wet granulation method. Carboxymethyl cellulose calcium and magnesium stearate are added to and mixed with the granules, and then the mixture was compressed into a tablet.

INDUSTRIAL APPLICABILITY

According to the present invention, the blood pressure lowering effect and patient compliance of an antidiabetic agent and an antihypertensive agent may be improved by formulating these agents in a single pharmaceutical composition.

What is claimed is:

1. A pharmaceutical composition comprising comprising an effective amount of a sodium glucose cotransporter-2 (SGLT-2) inhibitor and an effective amount of an angiotensin receptor blocker to control blood pressure,
   wherein the SGLT-2 inhibitor is dapagliflozin or a pharmaceutically acceptable salt or solvate thereof, and
   wherein the angiotensin receptor blocker is olmesartan, or a pharmaceutically acceptable salt thereof, or a pharmaceutically acceptable ester thereof.

2. The pharmaceutical composition of claim 1, wherein the pharmaceutical composition is a composition for treating a disorder comprising hypertension.

3. The pharmaceutical composition of claim 1, wherein the pharmaceutical composition is a composition for treating a disorder comprising hypertension and diabetes.

4. The pharmaceutical composition of claim 1, wherein the pharmaceutical composition is for administration to patients with a disorder comprising hypertension or patients with a disorder comprising both hypertension and diabetes.

5. The pharmaceutical composition of claim 1, wherein the pharmaceutical composition is a solid formulation.

* * * * *